United States Patent
Stüwe et al.

(10) Patent No.: US 6,468,399 B2
(45) Date of Patent: *Oct. 22, 2002

(54) PROCESS FOR ISOLATING CYCLOPENTANE AND/OR CYCLOPENTENE

(75) Inventors: Arnd Stüwe, Leverkusen; Rolf Dieter Wurtz, deceased, late of Herrenberg, by Helene Maria Wurtz, neé Paul and Peter Wurtz, legal representatives; Michael Müller; Jens Herwig, both of Köln; Christian Gabel; Joachim Grub, both of Dormagen, all of (DE)

(73) Assignee: BP Koln GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/784,853

(22) Filed: Feb. 16, 2001

(65) Prior Publication Data

US 2001/0020580 A1 Sep. 13, 2001

Related U.S. Application Data

(63) Continuation of application No. 09/264,145, filed on Mar. 5, 1999, now Pat. No. 6,264,799.

(30) Foreign Application Priority Data

Mar. 5, 1998 (DE) .......................... 198 09 361
Oct. 27, 1998 (DE) .......................... 198 49 425

(51) Int. Cl.[7] ............... B01D 3/00; C07C 5/03; C07C 7/04
(52) U.S. Cl. ............... 203/71; 203/29; 203/95; 203/98; 585/264; 585/800; 585/802
(58) Field of Search ............... 203/71, 78, 80, 203/29, 98, 99, 95, DIG. 19, 100; 585/374, 264, 802, 800, 364

(56) References Cited

U.S. PATENT DOCUMENTS 3,686,349 A * 8/1972 Schliebs et al. ............. 203/71
3,763,254 A * 10/1973 Engelhard et al. ............ 203/98
3,947,506 A * 3/1976 Lybarger ..................... 203/70
3,968,180 A * 7/1976 Kuppa et al. ................ 585/374
4,721,823 A * 1/1988 Venjer et al. ................ 585/359
6,100,435 A * 8/2000 Silverberg .................. 585/318

FOREIGN PATENT DOCUMENTS

| DE | 1643947 | 7/1971 |
| EP | 0 799 881 | 10/1997 |
| EP | 2256384 | 10/1997 |

OTHER PUBLICATIONS

Chemical Abstract EP 0 799 88.

* cited by examiner

Primary Examiner—Virginia Manoharan
(74) Attorney, Agent, or Firm—Connolly Bove Lodge & Hutz LLP (57) ABSTRACT

Cyclopentane and/or cyclopentene and, if desired, isopentane can be obtained by distillative separation from a prebenzene fraction or a $C_5$ fraction which has in each case being partially hydrogenated to remove acetylene compounds and diolefins, wherein a) in a first fractional distillation, low boilers are removed as first top product and, either b1) the first bottom product is fed to a second fractional distillation and there cyclopentene is taken off as second top product and cyclopentane and higher-boiling hydrocarbons are taken off as second bottom product and this second bottom product is separated into cyclopentene and higher boilers in a third fractional distillation, or b2) the first bottom product is subjected to a catalytic hydrogenation and subsequently, in a fractional distillation, separated into cyclopentane as top product and higher boilers as bottom product, or b3) the first bottom product is subjected to a fractional distillation to separate off the relatively high boilers as bottom product and the top product is subjected to a catalytic hydrogenation to form cyclopentene.

4 Claims, 4 Drawing Sheets

PROCESS FOR ISOLATING CYCLOPENTANE AND/OR CYCLOPENTENE

The present application is a continuation of application Ser. No. 09/264,145, filed Mar. 5, 1999, now U.S. Pat. No. 6,264,799, granted Jul. 24, 2001.

The present invention relate to a process for isolating cyclopentane and/or cyclopentene from a partially hydrogenated pre-benzene fraction or a partially hydrogenated $C_5$ fraction by distillative separation. In a variant of the process of the invention, isopentane (2-methylbutane) can be isolated in addition to cyclopentane.

In recent times, cyclopentane has become important as a replacement for chlorofluorocarbons (CFCs) as blowing agent for polyurethane systems since it may be regarded as harmless to the ozone layer of the earth's atmosphere. In addition, cyclopentane is of importance as a special solvent. Cyclopentene is a valuable comonomer for polymers and, in addition, can yield further cyclopentane by hydrogenation. Finally, isopentane is a valuable raw material for alkylates and other chemical reactions.

The cracking of naptha in steam crackers or in fluid catalytic crackers (FCCs) forms a tailgas (mainly $H_2$ and $CH_4$) plus valuable monomers such as ethylene, propene, 1-butene, 2-butene and isobutene and also butadiene ($C_2$, $C_3$ and $C_4$ fractions).

The remaining part of the cracker products, known as pyrolysis gasoline, is worked up for the recovery of aromatics. The pyrolysis gasoline is first partially hydrogenated in order to hydrogenate acetylene compounds and diolefins to form alkenes or monoolefins. Subsequently, a partially hydrogenated pre-benzene fraction is obtained from the partially hydrogenated pyrolysis gasoline by distillation. This partially hydrogenated pre-benzene fraction contains a large number of isomeric $C_5$-alkanes and $C_5$-alkenes, plus cyclopentane and cyclopentene, small amounts of incompletely removed $C_4$-hydrocarbons and a certain proportion of hydrocarbons having 6 or more carbon atoms. As an alternative, a partially hydrogenated $C_5$ fraction which contains a large number of isomeric $C_5$-alkanes and $C_5$-alkenes, cyclopentane, cyclopentene, small amounts of incompletely removed $C_4$-hydrocarbons and also small amounts of hydrocarbons having 6 or more carbon atoms can be obtained from the partially hydrogenated pyrolysis gasoline by distillation.

The work-up of the pyrolysis gasoline can also be carried out in such a way that a non-hydrogenated pre-benzene fraction is first obtained by distillative separation. This is subsequently partially hydrogenated, again in order to hydrogenate acetylene compounds and diolefins to form alkenes or monoolefins. This partially hydrogenated pre-benzene fraction then contains a large number of isomeric $C_5$-alkanes and $C_5$-alkenes, plus cyclopentane and cyclopentene, small amounts of incompletely removed $C_4$-hydrocarbons and a certain proportion of hydrocarbons having 6 or more carbon atoms. As an alternative, the work-up of the pyrolysis gasoline can also be carried out such that firstly only $C_5$-hydrocarbons are separated off by distillation, giving a non-hydrogenated $C_5$ fraction. This $C_5$ fraction is subsequently likewise hydrogenated and then contains a large number of isomeric $C_5$-alkanes and $C_5$-alkenes, cyclopentane, cyclopentene, small amounts of incompletely removed $C_4$-hydrocarbons and relatively small amounts of hydrocarbons having 6 or more carbon atoms.

A typical composition of a partially hydrogenated pre-benzene fraction or a partially hydrogenated $C_5$ fraction obtained by one of the above-described process variants is the following, where the sum of the percentages by weight is 100.

| Component (Hydrocarbons = HCs) | Content (% by weight) |
| --- | --- |
| $C_4$-HCs | 0–4 |
| Low-boiling $C_5$-HCs | 30–60 |
| 2-Methyl-2-butene | 8–20 |
| Cyclopentane | 6–24 |
| Cyclopentene | 8–27 |
| $C_6^+$-HCs | 0–25 |
| $C_5$-dienes | 0–0.5 |

The preferred composition of a partially hydrogenated pre-benzene fraction is the following, where the sum of the percentages by weight is 100.

| Component (Hydrocarbons = HCs) | Content (% by weight) |
| --- | --- |
| $C_4$-HCs | 0–3 |
| Low-boiling $C_5$-HCs | 30–45 |
| 2-Methyl-2-butene | 8–15 |
| Cyclopentane | 6–18 |
| Cyclopentene | 8–20 |
| $C_6^+$-HCs | 15–25 |
| $C_5$-dienes | 0–0.5 |

The preferred composition of a partially hydrogenated $C_5$ fraction is the following, where the sum of the percentages by weight is 100.

| Component (Hydrocarbons = HCs) | Content (% by weight) |
| --- | --- |
| $C_4$-HCs | 0–4 |
| Low-boiling $C_5$-HCs | 35–60 |
| 2-Methyl-2-butene | 9–20 |
| Cyclopentane | 7–24 |
| Cyclopentene | 9–27 |
| $C_6^+$-HCs | 0–2 |
| $C_5$-dienes | 0–0.5 |

EP-A-0 799 881 discloses carrying out a fractional distillation of partially hydrogenated pyrolysis gasoline for isolating cyclopentane and/or cyclopentene, where, if desired, a mixture of n-pentane and isopentane can be isolated by taking a mixture enriched in cyclopentane and cyclopentene from a side offtake of a column, taking of the remaining $C_5$ fraction at the top and obtaining hydrocarbons having 6 or more carbon atoms as bottoms. In the context of the process described in EP-A-0 799 881, unsaturated hydrocarbons can be subjected to catalytic hydrogenation. The disadvantage of this process is that a stream taken off at a side offtake of a first column into which a many-component mixture is fed is still a mixture of many components from which pure components can be isolated only by means of additional effort or only in unsatisfactory purity.

A further disadvantage of the process described in EP-A-0 799 881 is that the desired isopentane can only be obtained together with the less desired n-pentane. A further disadvantage of this process is that the position of the side offtake changes with fluctuating composition of the partially hydrogenated pyrolysis gasoline used as a result of the associated changes in the temperature profile of the column, so that optimal recovery of cyclopentane and/or cyclopentene is not possible.

It has now been found that it is better from the points of view of energy consumption and the quality of the desired materials which can be obtained, i.e. for economic reasons, to provide separate distillation steps and to provide a side offtake only in a final distillation column, although a person skilled in the art would have to regard such a procedure as too complicated.

The invention relates to a process for isolating cyclopentane and/or cyclopentene by distillative separation of a partially hydrogenated pre-benzene fraction or a partially hydrogenated $C_5$ fraction, which is characterized in that a) in a first fractional distillation of the partially hydrogenated pre-benzene fraction or the partially hydrogenated $C_5$ fraction low boilers having boiling points below that of cyclopentene are taken off as first top product and high boilers comprising cyclopentene and hydrocarbons having boiling points higher than that of cyclopentene are taken off as first bottom product and, either, b1) the first bottom product is fed to a second fractional distillation and there cyclopentene is taken off as second top product and cyclopentane together with hydrocarbons having boiling points higher than that of cyclopentane is taken off as second bottom product and this second bottom product is subjected to a third fractional distillation where cyclopentane is isolated as third top product and hydrocarbons having boiling points higher than that of cyclopentane are separated off as third bottom product, or b2) the first bottom product is subjected to a catalytic hydrogenation and is subsequently separated in a fractional distillation into cyclopentane as top product and hydrocarbons having boiling points higher than that of cyclopentane as bottom product, or b3) the first bottom product is subjected to a fractional distillation where the hydrocarbons having boiling points higher than that of cyclopentane are separated off as bottom product and the top product is subjected to a catalytic hydrogenation to give cyclopentane.

The typical compositions of the partially hydrogenated pre-benzene fraction or the partially hydrogenated $C_5$ fraction correspond to those given above.

Figure 2:
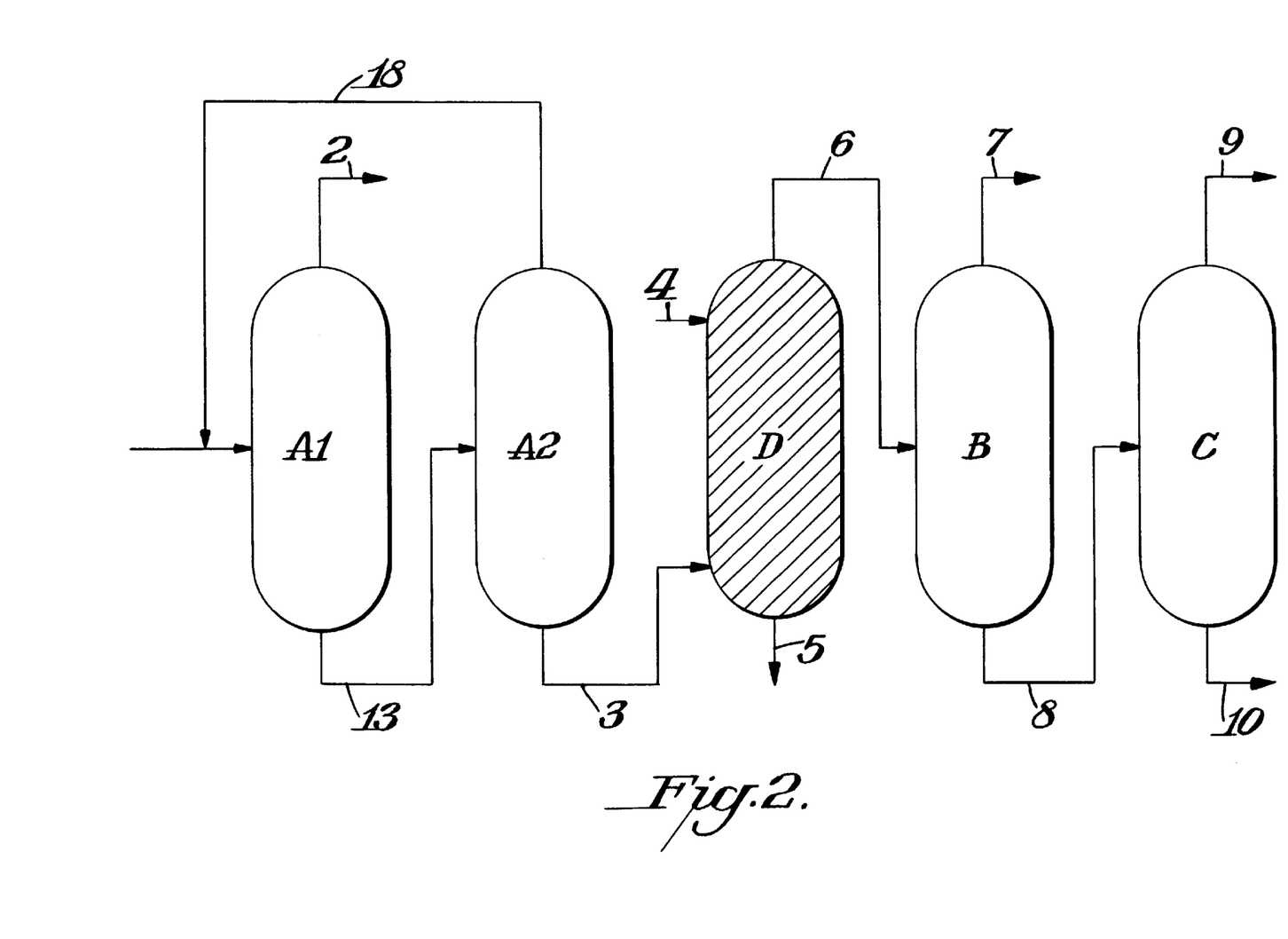

In the process of the invention, low boilers having boiling points below that of cyclopentene are separated off as first top product in a first fractional distillation according to step a). This first fractional distillation can be carried out, for example, in one stage in which a column with sufficient separation efficiency for virtually complete removal of the low boilers is provided. However, it is likewise possible to carry out the first fractional distillation in two stages, in which case an increased concentration of low boilers can then be permitted in the bottoms of the first stage and these low boilers are completely distilled out in the second stage. The low boilers from the second stage can contain higher boilers and are advantageously returned to the inlet of the first stage (FIG. 2).

Depending on whether the first fractional distillation according to step a) has been carried out in one or two stages, the bottom product of the first or second stage is fed to a further fractional distillation according to b1) or treated further according to b2) or b3). If the bottom product from step a) is fed to the second fractional distillation according to embodiment b1), cyclopentene is obtained in high purity as second top product and cyclopentane and hydrocarbons having boiling points higher than that of cyclopentane are obtained as second bottom product. The second bottom product is subsequently, in a third fractional distillation, separated into cyclopentane as third top product and hydrocarbons having 6 or more carbon atoms and boiling points higher than that of cyclopentane as third bottom product.

In the variant b2), the bottom product of the first fractional distillation (carried out in one or two stages) is fed to a catalytic hydrogenation to convert olefins into saturated hydrocarbons. In particular, cyclopentene is here converted into the cyclopentane desired as blowing gas and the yield of the latter is thus increased. Subsequent to the catalytic hydrogenation, the second fractional distillation is omitted and the hydrogenation product is separated into cyclopentane as top product and the hydrocarbons having boiling points higher than that of cyclopentene as bottom product.

This order of variant b2), namely first carrying out the catalytic hydrogenation and subsequently carrying out a fractional distillation, can also, according to variant b3), be reversed. In this case, the hydrocarbons having boiling points higher than cyclopentane are first, in a fractional distillation, separated off as bottom product from the first bottom product from step a) and the top product is then subjected to a catalytic hydrogenation to produce cyclopentane from cyclopentene.

In addition to the isolation of cyclopentane, the variant b2) also allows the additional isolation of isopentane.

The invention thus also provides a process for isolating cyclopentane and additionally isopentane by distillative separation of a partially hydrogenated pre-benzene fraction or a partially hydrogenated $C_5$ fraction, which is characterized in that a) in a first fractional distillation of the partially hydrogenated pre-benzene fraction or the partially hydrogenated $C_5$ fraction, low boilers having boiling points below that of 2-methyl-2-butene are taken off as first top product and high boilers comprising 2-methyl-2-butene and hydrocarbons having boiling points higher than that of 2-methyl-2-butene are taken off as first bottom product and b2) the first bottom product is subjected to a catalytic hydrogenation and is subsequently, in a fractional distillation, separated into isopentane as top product, cyclopentane as side stream and hydrocarbons having 6 or more carbon atoms as bottom product.

Here, the isopentane is obtained as a pure product and, in particular, is not accompanied by n-pentane which allows direct use in alkylation processes or another application.

The additional isolation of isopentane is also possible by means of variant b3).

The invention therefore also provides a process for isolating cyclopentane and additionally isopentane by distillative separation of a partially hydrogenated pre-benzene fraction or a partially hydrogenated $C_5$ fraction, characterized in that a) in a first fractional distillation of the partially hydrogenated pre-benzene fraction or the partially hydrogenated C$_5$ fraction, low boilers having boiling points below that of 2-methyl-2-butene are taken off as first top product and high boilers comprising 2-methyl-2-butene and hydrocarbons having boiling points higher than that of 2-methyl-2-butene are taken off as first bottom product and b3) the first bottom product is fractionally distilled to separate off the relatively high boilers in the form of hydrocarbons having 6 or more carbon atoms as bottom product and the top product containing essentially cyclopentene, cyclopentane and 2-methyl-2-butene is first catalytically hydrogenated to form isopentane and cyclopentane and subsequently separated by fractional distillation into isopentane as top product, cyclopentane as side stream and hydrocarbons having 6 or more carbon atoms as bottom product.

In this process, however, only traces of the relatively high boilers are obtained at the end.

Figure 3:
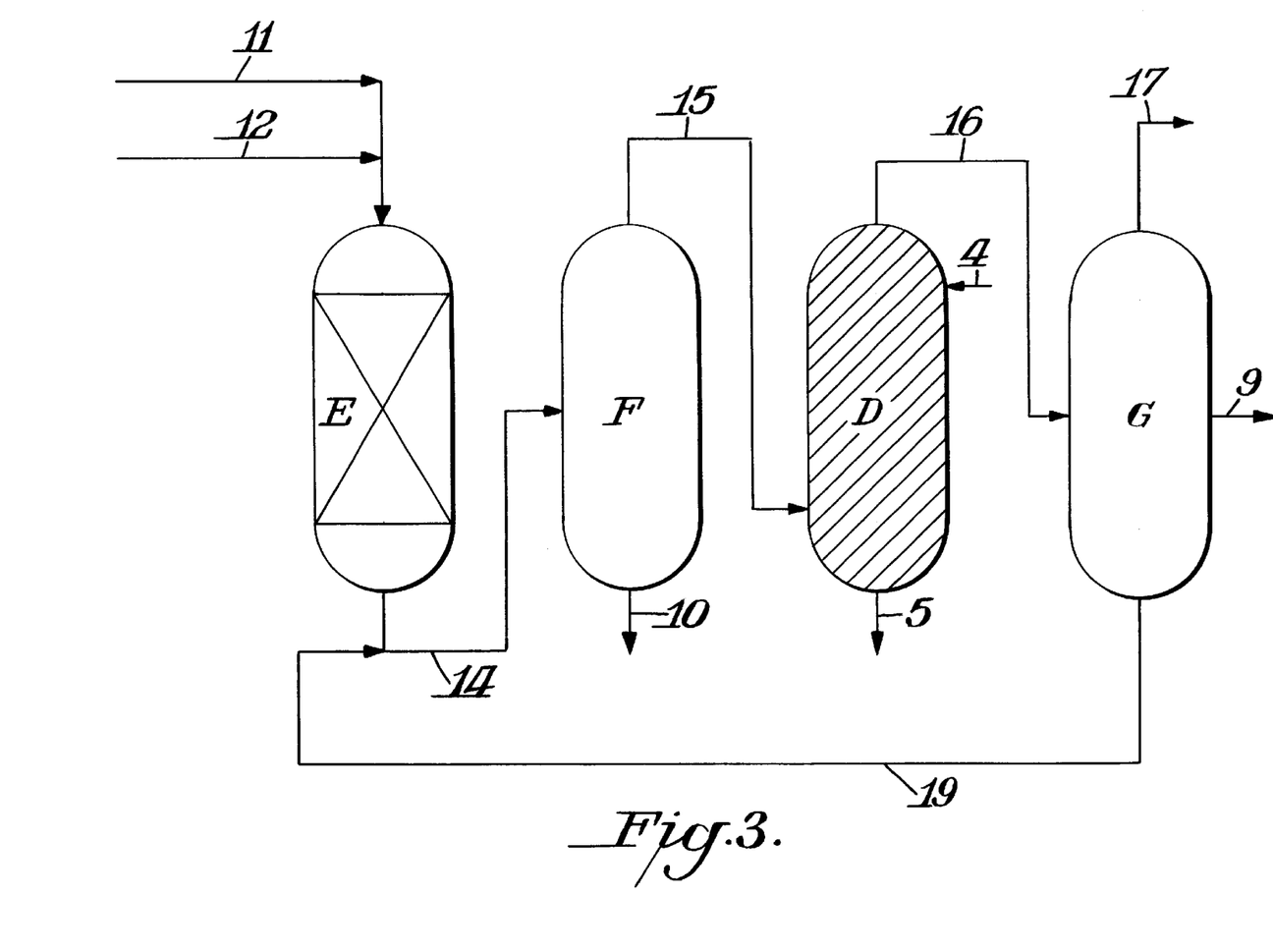

Distillation bottoms which have not been completely freed of lower-boiling fractions in the various fractional distillations of the process of the invention in order to produce pure top products can be recirculated to the process of the invention at an appropriate point, as is shown by way of example in FIG. 3. The distillation bottoms comprising hydrocarbons having 6 or more carbon atoms which are to be finally discharged after carrying out the process of the invention can be used in an appropriate way in an integrated petrochemical plant, for example as return stream to a cracker.

In a further, preferred embodiment of the process of the invention removal of oxygen-containing organic compounds can be carried out at a suitable point by subjecting the mixture of the hydrocarbons to be fractionated to a water scrub. The oxygen-containing organic compounds are then present in the wastewater flowing out as bottom product from such a scrub and this wastewater is subjected to biological purification or another method of disposal. Preferably, this water scrub is carried out immediately before the fine distillation to give the desired products.

When carrying out the process of the invention according to variant a) and b1), the water scrub preferably takes place between the first and second fractional distillations.

If the process of the invention is carried out using the variant a) and b2) or a) and b3), the water scrub is preferably carried out before or after the catalytic hydrogenation.

If the variants a) and b2) or a) and b3) are carried out so as to additionally isolate isopentane, it has been found to be particularly useful to carry out the water scrub immediately before the final fractional distillation.

The process of the invention is particularly suitable for use of partially hydrogenated pre-benzene fractions which have the abovementioned composition. However, due to the separately carried out fractional distillation steps according to the above description, it is also suitable for pre-benzene fractions which are characterized by proportions of low boilers and/or high boilers which deviate from those indicated above. This makes it possible, for example, to use bought-in pre-benzene fractions which come from a different petrochemical plant and therefore have greatly different compositions.

In the process of the invention, suitable fractional distillation columns are those which are known to those skilled in the art. Accordingly, they can contain distillation trays of the various known types, loose column packing of the various known types or structured packing of the various known types. The matching of such columns to the requirements of the various fractional distillation steps of the process of the invention is known in principle and requires no further explanation. In a particular embodiment, the final step of the variant of the process of the invention with additional isolation of isopentane, where the cyclopentane is taken off as a side stream, can be carried out in a dividing wall column.

The process of the invention can be carried out essentially regardless of the applied pressure. However, since the materials isolated in the process of the invention are characterized by low boiling points at atmospheric pressure, particularly as regards the respective top products, efforts will be made to avoid using expensive cooling brine or likewise expensive chilled water for condensing the top products, but rather to use normal cooling water as far as possible for condensation. To achieve this, use is made of superatmospheric pressure to increase the condensation temperatures. This superatmospheric pressure is in the range from 1.5 to 10 bar absolute.

The catalytic hydrogenation provided for in the process variants b2) and b3) is carried out under conditions which are essentially known. As hydrogenation catalysts, use is made of noble metals, for instance palladium, platinum, ruthenium or rhodium, or nickel, with or without known promoters, applied to supports. Suitable catalyst supports are $Al_2O_3$, $SiO_2$, activated carbon or other support materials suitable for these purposes. Suitable temperatures for the hydrogenation are in the range from 20 to 200° C., preferably from 20 to 60° C., in the case of platinum metals and from 120 to 180° C. in the case of nickel. Low temperatures within these ranges are preferred because the product stream from the hydrogenation then does not have to be cooled at high cost. The $H_2$ pressure in the catalytic hydrogenation is in the range from 5 to 100 bar, preferably from 5 to 30 bar. The hydrogen used can be either pure hydrogen or tailgas which is available in petrochemical plants and in many cases consists of about 70% of $H_2$, 25% of $CH_4$ and small amounts of further constituents which are inert to hydrogenation.

Among the numerous embodiments of the process of the invention, a few are shown by way of example in FIGS. 1, 2, 3 and 4. In these figures, pumps, heat exchangers, condensers, heating devices and pressure control devices are not shown for the sake of greater clarity. The same symbols refer to the same equipment items or the same streams.

Figure 1:
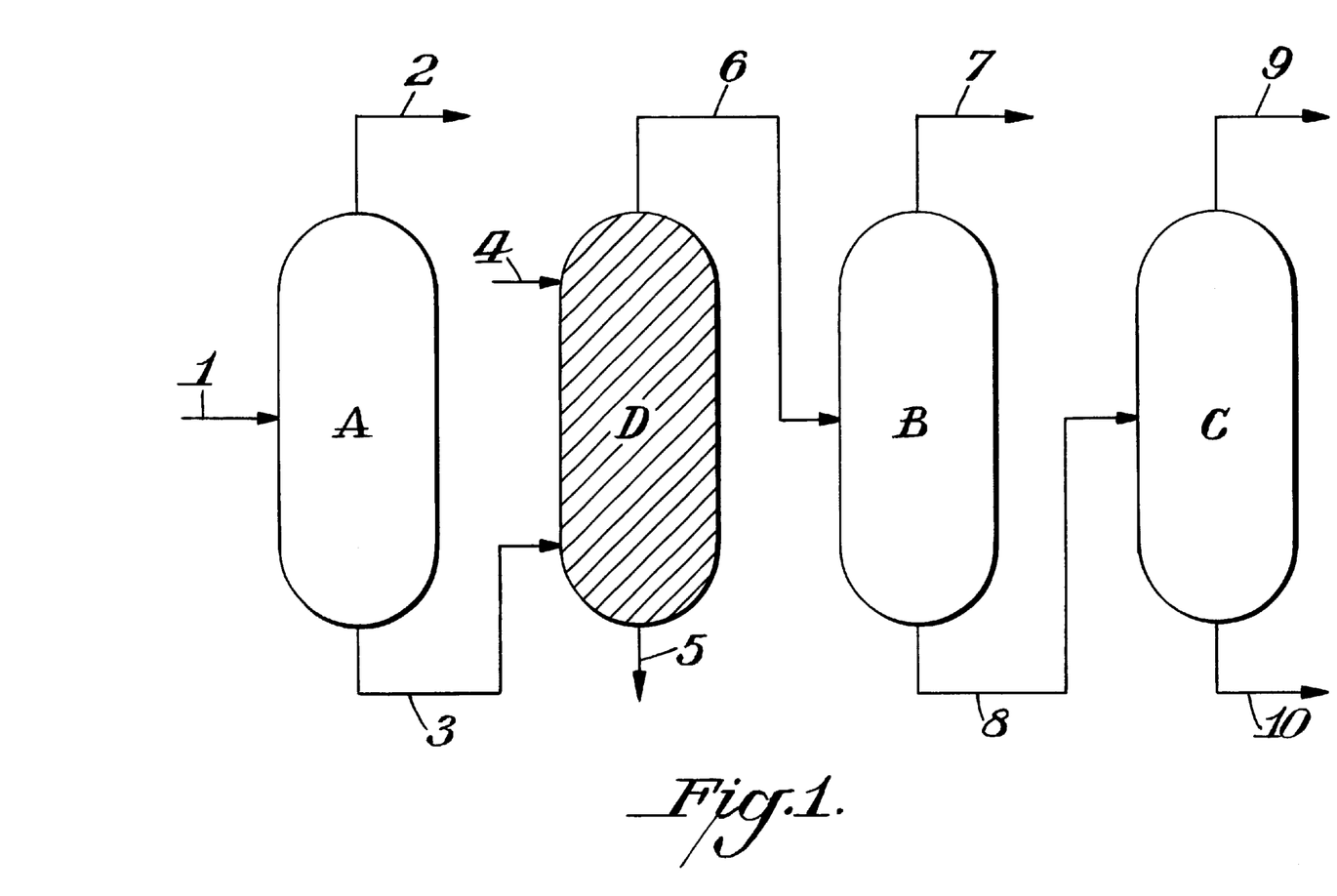
FIGS. 1–4 comprise diagrammatic flow diagrams 1 according to the present invention.

FIG. 1 shows three distillation columns A, B and C for the first, second and third fractional distillations according to embodiment a) and b1). D is a column for carrying out the water scrub which is preferably employed.

The streams in FIG. 1 are as follows:
1=partially hydrogenated pre-benzene fraction or partially hydrogenated C$_5$ fraction
2=first top product comprising low boilers having boiling points below that of cyclopentene,
3=first high-boiling bottom product comprising cyclopentene and components having boiling points higher than that of cyclopentene, 4=water for scrubbing,
5=wastewater from the water scrub,
6=first bottom product from A after scrubbing with water,
7=cyclopentene as second top product,
8=second bottom product,
9=cyclopentane and
10=third bottom product comprising hydrocarbons having 6 or more carbon atoms.

FIG. 2 shows a variant in which the first fractional distillation is carried out in two stages: For this reason, the first distillation column A is replaced by two distillation columns A1 and A2, which can also be operated as different sections of one column. The two columns are connected to one another such that a bottom product 13 from A1 is fed into A2 and the top product from A2 is returned as return stream 18 to the inlet of A1. All other streams have the meanings explained in connection with FIG. 1.

FIG. 3 shows an embodiment which includes a catalytic hydrogenation according to b2) and which allows the additional isolation of isopentane in pure form. Here too, a water scrub is provided in column D. Otherwise, FIG. 3 contains the hydrogenation reactor E and two distillation columns F and G. In E, the first bottom product 12 from the first fractional distillation, which contains 2-methyl-2-butene as a further material in addition to the materials present in the streams 3 and 13 in FIGS. 1 and 2, is hydrogenated. In addition, $H_2$ is introduced into E as stream 11. The outflow 14 from E contains essentially only saturated hydrocarbons in this embodiment and is introduced into F. In this embodiment, F assumes the function of C in FIGS. 1 and 2 as regards the removal of hydrocarbons having 6 or more carbon atoms. The top product 15 from F is fed to a water scrub in D. The top product 16 from D contains isopentane, cyclopentane and small amounts of hydrocarbons having 6 or more carbon atoms which have not been removed completely in the distillation and is fed to the distillation column G. Cyclopentane 9 is taken off from G at a side offtake and isopentane 17 is taken off from G as top product.

The bottoms stream 19 from G contains the hydrocarbons having 6 or more carbon atoms and is combined with stream 14.

Figure 4:
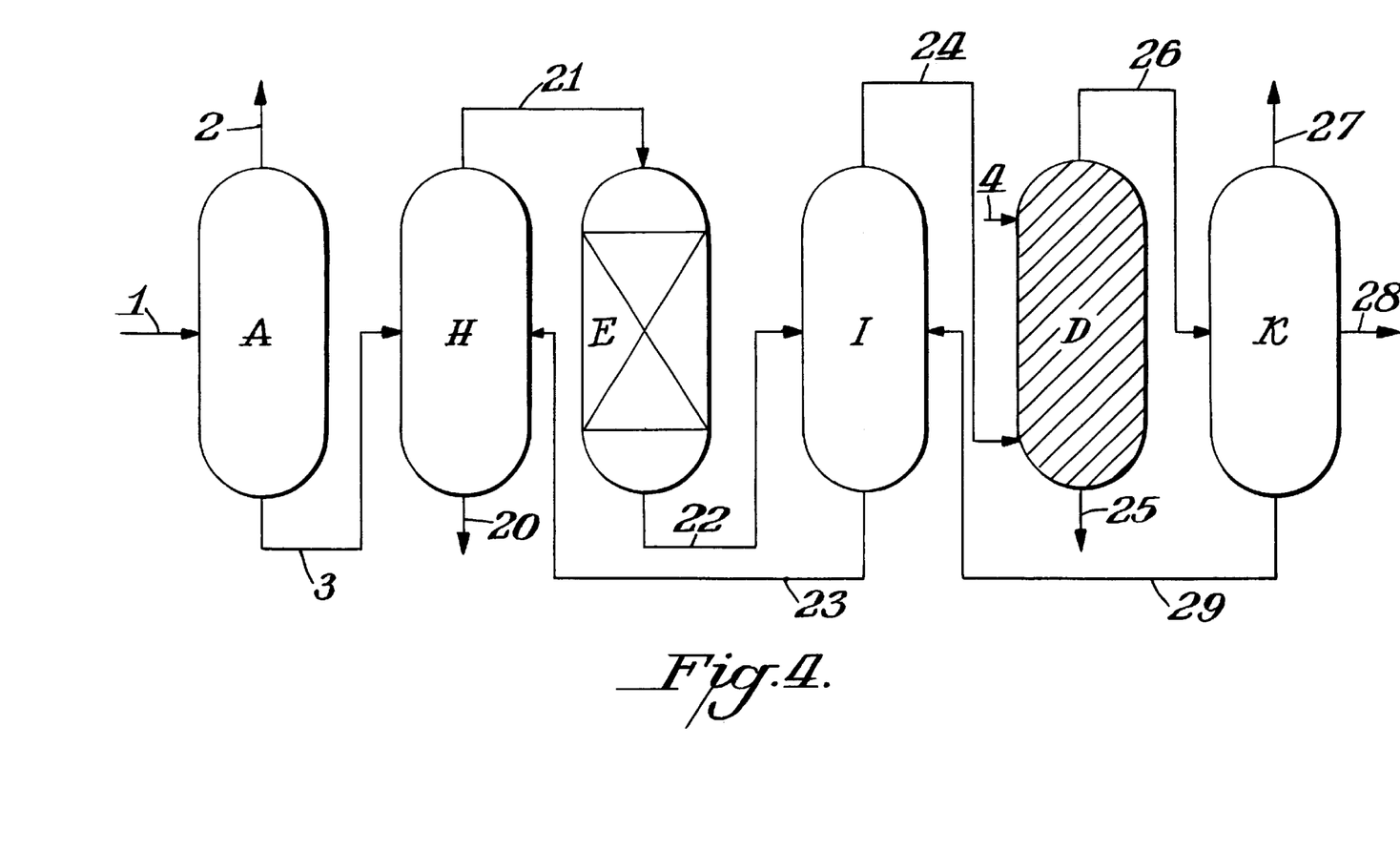

FIG. 4 shows an embodiment in which the first fractional distillation according to step a) is first carried out in one stage and the first bottom product 3 is subsequently, according to variant b3), subjected to a further fractional distillation in distillation column H, where the relatively high boilers 20 are separated off as bottom product. The top product 21 contains predominantly cyclopentene and cyclopentane and is catalytically hydrogenated in reactor E, giving a crude cyclopentane fraction as outflow 22. This is subjected to a further fractional distillation in distillation column I. The higher boilers of this fractional distillation 23 are recirculated to the fractional distillation H, while the top product 24 is fed to a water scrub in column D. The top product 26 contains essentially only cyclopentane and is subjected to a final fine distillation in distillation column K, with the pure cyclopentane being taken off as side stream 28.

EXAMPLE

In a first distillation column having about 20 theoretical plates, 100 parts of pre-benzene fraction typically give, at a reflux of 750 parts, about 58 parts of top product and 42 parts of bottom product with the top product containing less than 4 parts of cyclic $C_5$-hydrocarbons (cyclopentane and cyclopentene). The bottom product obtained consists of about 20 parts of the cyclic $C_5$-hydrocarbons, about 1 part of 2-methyl-2-butene, accompanied by traces of pentenes and about 21 parts of hydrocarbons having 6 or more carbon atoms. The bottom product obtained is, without further purification, passed to a hydrogenation reactor in which hydrogen is fed in and the unsaturated compounds are converted into saturated compounds over a commercially available hydrogenation catalyst based on noble metal or nickel. In a downstream second column having about 50 theoretical plates, the 42 parts of the hydrogenated bottom product are further fractionated by distillation at a reflux of about 80 parts. This gives about 22 parts of second top product and about 20 parts of second bottom product. The second top product contains about 19 parts of cyclopentane in admixture with about 2 parts of isopentane (from the hydrogenation of 2-methyl-2-butene) and about 1 part of higher hydrocarbons. Only small amounts (about 1 part) of cyclopentane are lost in the bottom product. The bottom product thus consists virtually exclusively of hydrocarbons having 6 or more carbon atoms and can, for example, be used as a petrol component or as petroleum ether (solvent). The second top product is subsequently freed of small amounts of oxygen-containing polar impurities present therein by means of a water scrub. Finally, in a fine purification column, the cyclopentane is concentrated up by distillation to a purity of typically from 95 to 99% by weight. This last distillation column having about 70 theoretical plates separates, at a reflux of about 50 parts, the 22 parts of the top product from the $H_2O$ scrub into 2 parts of top product (isopentane), 18 parts of cyclopentane of the purity indicated (side stream) and about 2 parts of bottom product comprising only small amounts of cyclopentane and mainly hydrocarbons having 6 or more carbon atoms. The latter bottom product is recirculated to the outflow from the hydrogenation reactor in order to increase the yield.

What is claimed is:

1. Process for isolating cyclopentane and/or cyclopentene by distillative separation of a partially hydrogenated pre-benzene fraction or a partially hydrogenated $C_5$ fraction including cyclopentene and cyclopentane, consisting essentially of the steps of a) taking off as first top product low boilers having boiling points below that of cyclopentene in a first fractional distillation of the partially hydrogenated pre-benzene fraction or the partially hydrogenated $C_5$ fraction, and taking off as first bottom product high boilers comprising cyclopentene and hydrocarbons having boiling points higher than that of cyclopentene, and cyclopentane and hydrocarbons having boiling points higher than that of cyclopentane and, either b1) feeding the first bottom product to a second fractional distillation and taking off cyclopentene as second top product and taking off as a second bottom portion cyclopentane together with hydrocarbons having boiling points higher than that of cyclopentane, and subjecting this second bottom product to a third fractional distillation where cyclopentane is isolated as third top product and separating off as third bottom product hydrocarbons having boiling points higher than that of cyclopentane, or b2) subjecting the first bottom product to a catalytic hydrogenation and subsequently separated the catalytic hydrogenation product in a fractional distillation into cyclopentane as top product and hydrocarbons having boiling points higher than that of cyclopentane as bottom product, or b3) subjecting the first bottom product to a second fractional distillation, separating off as second bottom product the hydrocarbons having boiling points higher than that of cyclopentane and subjecting then the top product to a catalytic hydrogenation to give cyclopentane, and optionally c) subjecting the fraction, the top product, or the bottom product in any one of steps a), b1), b2), and b3) to a water scrub.

2. Process according to claim 1, wherein the first fractional distillation is carried out in two stages, where the low boilers are taken off as top product in the first stage, the bottom product of the first stage is transferred completely to the second stage, and the top product of the second stage is recirculated to an inlet of the first stage.

3. Process according to claim 1, wherein the partially hydrogenated pre-benzene fraction or the partially hydrogenated $C_5$ fraction has the following composition, where the sum of the percentages by weight is 100:

| Component (Hydrocarbons = HCs) | Content (% by weight) |
|---|---|
| $C_4$-HCs | 0–4 |
| Low-boiling $C_5$-HCs | 30–60 |
| 2-Methyl-2-butene | 8–20 |
| Cyclopentane | 6–24 |
| Cyclopentene | 8–27 |
| $C_6^+$-HCs | 0–25 |
| $C_5$-dienes | 0–0.5. |

4. Process according to claim 1, wherein a water scrub is carried out and the water scrub is carried out between the first and second fractional distillations.

* * * * *

UNITED STATES PATENT AND TRADEMARK OFFICE
CERTIFICATE OF CORRECTION

PATENT NO.    : 6,468,399 B2
DATED         : October 22, 2002
INVENTOR(S)   : Arnd Stüwe et al.

It is certified that error appears in the above-identified patent and that said Letters Patent is hereby corrected as shown below:

<u>Column 8,</u>
Line 60, delete "a".
Line 60, delete "portion" and insert -- product --.

<u>Column 9,</u>
Line 2, delete "separated" and insert -- separating --.

Signed and Sealed this

Eleventh Day of February, 2003

JAMES E. ROGAN
*Director of the United States Patent and Trademark Office*